United States Patent
Mohika et al.

(12)

(10) Patent No.: US 9,664,213 B2
(45) Date of Patent: May 30, 2017

(54) SYSTEM FOR CONTAINMENT AND ORGANIZATION OF MEDICAL WIRE

(71) Applicant: Cook Medical Technologies LLC, Bloomington, IN (US)

(72) Inventors: Brian O. Mohika, Lawrence, MA (US); John A. Brumleve, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/808,659

(22) Filed: Jul. 24, 2015

(65) Prior Publication Data

US 2016/0053784 A1    Feb. 25, 2016

Related U.S. Application Data

(63) Continuation-in-part of application No. 14/512,939, filed on Oct. 13, 2014, now Pat. No. 9,499,318.
(Continued)

(51) Int. Cl.
*B65D 67/02* (2006.01)
*F16B 2/10* (2006.01)
(Continued)

(52) U.S. Cl.
CPC ............. *F16B 2/10* (2013.01); *A61B 17/0487* (2013.01); *A61B 17/122* (2013.01); *A61B 50/20* (2016.02);
(Continued)

(58) Field of Classification Search
CPC ......... Y10T 24/44556; Y10T 24/44654; Y10T 24/44444; Y10T 24/44564; B65D 67/02;
(Continued)

(56) References Cited

U.S. PATENT DOCUMENTS

| 3,503,397 A | 3/1970 | Fogarty et al. |
| 3,503,398 A | 3/1970 | Fogarty et al. |

(Continued)

FOREIGN PATENT DOCUMENTS

| WO | WO 00/06030 | 2/2000 |
| WO | WO 2004/066846 A1 | 8/2004 |

(Continued)

OTHER PUBLICATIONS

Extended European Search Report, dated Jan. 20, 2016, pp. 1-12, issued in European Patent Application No. 15180264.2-1654, European Patent Office, Munich, Germany.
(Continued)

*Primary Examiner* — Robert J Sandy
(74) *Attorney, Agent, or Firm* — Brinks Gilson & Lione

(57) ABSTRACT

A system for containment and organization of a medical wire features a clamp. A first ridged and grooved clamping block is located on a clamp first side posterior end and a second ridged and grooved clamping block is located on a clamp second side posterior end. A first side compression member is located on an inside surface of a clamp first side and a second side compression member is located on an inside surface of the clamp second side. An adjustable ratcheting lock attaches the clamp first side and the clamp second side. A first finger grip is located on an outside surface of the clamp first side and a second finger grip is located on an outside surface of the clamp second side. A Medical wire is placed between the first side compression member and the second side compression member then the clamp is compressed against the medical wire.

20 Claims, 4 Drawing Sheets

Related U.S. Application Data

(60) Provisional application No. 62/040,305, filed on Aug. 21, 2014.

(51) Int. Cl.
*A61B 17/04* (2006.01)
*A61B 17/122* (2006.01)
*A61B 90/90* (2016.01)
*A61B 50/20* (2016.01)
A61B 17/00 (2006.01)
A61B 17/28 (2006.01)

(52) U.S. Cl.
CPC .............. *A61B 90/90* (2016.02); *B65D 67/02* (2013.01); *A61B 2017/00407* (2013.01); *A61B 2017/00858* (2013.01); *A61B 2017/2825* (2013.01); *Y10T 24/44444* (2015.01); *Y10T 24/44556* (2015.01); *Y10T 24/44564* (2015.01)

(58) Field of Classification Search
CPC ................ A61B 17/28; A61B 17/1214; A61B 2017/2808; A61M 25/002; A61M 2025/09125
See application file for complete search history.

(56) References Cited

U.S. PATENT DOCUMENTS

| | | | |
|---|---|---|---|
| 3,604,071 A | 9/1971 | Reimels | |
| 4,835,824 A | 6/1989 | Durham et al. | |
| 4,896,465 A * | 1/1990 | Rhodes ............... | A61M 5/1418 128/849 |
| 4,971,271 A * | 11/1990 | Sularz .................... | F16L 3/223 248/229.13 |
| 5,022,126 A | 6/1991 | Davis | |
| D333,182 S | 2/1993 | Yoshikawa | |
| 5,226,892 A * | 7/1993 | Boswell ............... | A61M 5/1418 128/DIG. 26 |
| 5,489,287 A | 2/1996 | Green et al. | |
| 5,573,541 A | 11/1996 | Green et al. | |
| 5,591,182 A | 1/1997 | Johnson | |
| 5,944,729 A | 8/1999 | Blake | |
| 6,099,539 A | 8/2000 | Howell et al. | |
| 6,206,896 B1 | 3/2001 | Howell et al. | |
| 6,228,104 B1 | 5/2001 | Fogarty et al. | |
| 6,273,902 B1 | 8/2001 | Fogarty et al. | |
| 6,293,954 B1 | 9/2001 | Fogarty et al. | |
| 6,299,621 B1 | 10/2001 | Fogarty et al. | |
| 6,387,106 B1 | 5/2002 | Howell et al. | |
| 6,387,112 B1 | 5/2002 | Fogarty et al. | |
| 6,406,485 B1 | 6/2002 | Hossain et al. | |
| 6,460,231 B2 | 10/2002 | Bourgerie | |
| 6,530,942 B2 | 3/2003 | Fogarty et al. | |
| 6,558,408 B1 | 5/2003 | Fogarty et al. | |
| 6,579,304 B1 | 6/2003 | Hart et al. | |
| 6,626,922 B1 | 9/2003 | Hart et al. | |
| 6,692,514 B2 | 2/2004 | Fogarty et al. | |
| 6,719,766 B1 | 4/2004 | Buelna et al. | |
| 6,821,284 B2 | 11/2004 | Sturtz et al. | |
| 6,942,676 B2 | 9/2005 | Buelna | |
| 6,989,017 B2 | 1/2006 | Howell et al. | |
| 7,322,995 B2 | 1/2008 | Buckman et al. | |
| 7,578,827 B2 | 8/2009 | Gadberry et al. | |
| 7,780,688 B2 | 8/2010 | Sakakine et al. | |
| 7,850,702 B2 | 12/2010 | Sorribes | |
| 8,092,473 B2 | 1/2012 | Hart et al. | |
| 8,167,252 B2 | 5/2012 | Nitsche et al. | |
| 8,201,310 B1 | 6/2012 | Abdi et al. | |
| 8,273,102 B2 | 9/2012 | Danitz et al. | |
| 8,578,571 B2 | 11/2013 | Schmidt et al. | |
| 2002/0007538 A1* | 1/2002 | Bourgerie ............. | A01K 97/08 24/517 |
| 2011/0210215 A1 | 9/2011 | Nitsche et al. | |
| 2011/0313437 A1 | 12/2011 | Yeh | |
| 2013/0212844 A1 | 8/2013 | Chen | |

FOREIGN PATENT DOCUMENTS

| | | |
|---|---|---|
| WO | WO 2005/048854 A2 | 6/2005 |
| WO | WO 2005/096960 A1 | 10/2005 |
| WO | WO 2016/133962 A1 | 8/2016 |

OTHER PUBLICATIONS

Medline Industries, Inc., "OR Necessities® Separate Sterile Pack Components" catalog, dated 2011, p. 25, Mundelein, IL.
Cook Medical Technologies LLC, "Clip", at least as early as Aug. 20, 2014, 2 pgs.

* cited by examiner

SYSTEM FOR CONTAINMENT AND ORGANIZATION OF MEDICAL WIRE

CROSS REFERENCE

This application is a continuation in part of U.S. patent application Ser. No. 14/512,939 filed Oct. 13, 2014, which claims the benefit of U.S. Provisional Patent Application No. 62/040,305 filed Aug. 21, 2014, the specifications of which are incorporated herein in their entirety by reference.

FIELD

The present disclosure relates to medical devices, systems, and methods, and more specifically, medical wire devices, medical wire systems, and methods of containing and organizing medical wire.

BACKGROUND

Wire used for medical purposes is carefully manufactured, sterilized, and sealed in a sterilized package in preparation for use. Once removed from the package, this wire can be difficult to handle and keep separate from other medical wires of a different size, especially in a pressure-filled environment. It can even be slippery at times. The present disclosure features a system and method for containment and organization of medical wire.

Any feature or combination of features described herein are included within the scope of the present disclosure provided that the features included in any such combination are not mutually inconsistent as will be apparent from the context, this specification, and the knowledge of one of ordinary skill in the art. Additional advantages and aspects are apparent in the following detailed description and claims.

SUMMARY

The present disclosure features a system for containment and organization of medical wire. In some embodiments, the system comprises a clamp. In some embodiments, the clamp comprises a shape of a "U". In some embodiments, a first ridged and grooved clamping block is angularly located on a clamp first side posterior end and a second ridged and grooved clamping block is angularly located on a clamp second side posterior end. In some embodiments, the first ridged and grooved clamping block interfaces with the second ridged and grooved clamping block upon closure of the clamp.

In some embodiments, the system comprises a first side compression member. In some embodiments, the first side compression member is located on an inside surface of a clamp first side next to the first ridged and groove clamping block and projects out and away from the clamp first side toward a clamp second side. In some embodiments, the first side compression member comprises a shape of a rectangular prism. In some embodiments, the first side compression member is elastomeric.

In some embodiments, the system comprises a second side compression member. In some embodiments, the second side compression member is located on an inside surface of the clamp second side next to the second ridged and groove clamping block and projects out and away from the clamp second side toward the clamp first side. In some embodiments, the second side compression member comprises a shape of a rectangular prism. In some embodiments, the second side compression member is elastomeric.

In some embodiments, the system comprises an adjustable ratcheting lock located between and attaching the clamp first side and the clamp second side. In some embodiments, a ratcheting lock first end is located on the inside surface of the clamp first side between the clamp first side posterior end and a clamp anterior end and a ratcheting lock second end is located on the inside surface of the clamp second side between the clamp second side posterior end and the clamp anterior end.

In some embodiments, the system comprises a first finger grip located on an outside surface of the clamp first side opposed to the ratcheting lock first end and a second finger grip located on an outside surface of the clamp second side opposed to the ratcheting lock second end.

In some embodiments, medical wire is placed in an open clamp between the first side compression member and the second side compression member. In some embodiments, the clamp is closed having the first ridged and grooved clamping block interlocked against the second ridged and grooved clamping block. In some embodiments, the adjustable ratcheting lock is tightened via manually pinching the clamp via the first finger grip and the second finger grip to compress the first side compression member and the second side compression member against the medical wire for securely holding into position.

DESCRIPTION OF PREFERRED EMBODIMENTS

Figure 1:
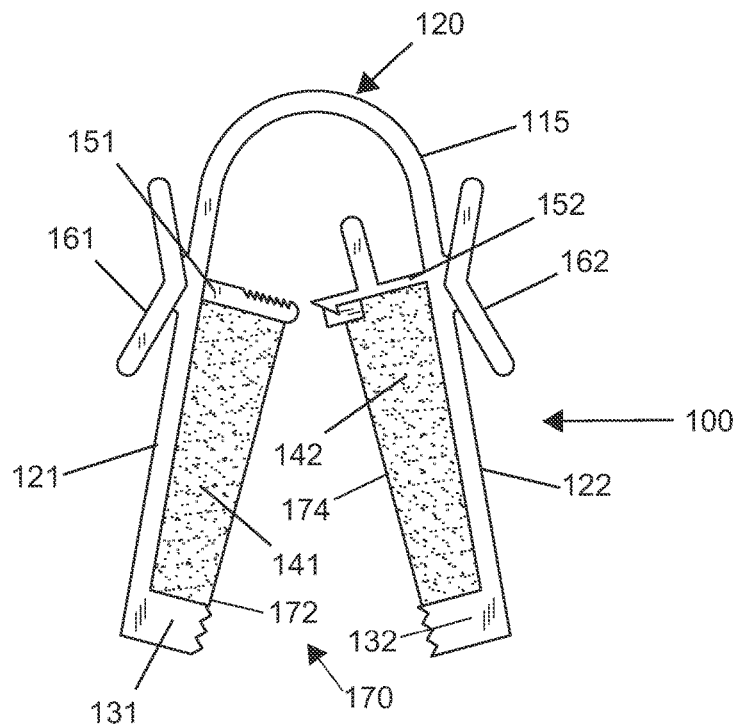
FIG. 1 shows a front view of one embodiment of the present invention, in the open position.

A list of possible elements shown in the drawings and corresponding to elements described below are included herein:

100 Medical wire containment and organization system
110 Medical wire
115 Body
120 Clamp
121 Clamp first side
122 Clamp second side
123 Clamp first side posterior end
124 Clamp second side posterior end
125 Clamp anterior end
126 Clamp posterior end
131 First ridged and grooved clamping block
132 Second ridged and grooved clamping block
141 First side compression member
142 Second side compression member 150 Ratcheting lock
151 Ratcheting lock first end
152 Ratcheting lock second end
161 First finger grip
162 Second finger grip
170 Gap
172 First surface
174 Second surface
182 Groove
184 Ridge
190 First material
192 Second material
194 Minimum width for wedge-shaped compression member
196 Maximum width for wedge-shaped compression member Referring now to FIG. 1-6, one embodiment of the present invention features a system (100) for containment and organization of medical wire. In some embodiments, the system (100) comprises a clamp (120) having a clamp first side (121), a clamp second side (122), a clamp anterior end (125), and a clamp posterior end (126). In some embodiments, the clamp (120) may comprise a shape of a "U". In some embodiments, the clamp (120) may comprise a terminating clamp first side posterior end (123) located on the clamp first side (121) at the clamp posterior end (126), a terminating clamp second side posterior end (124) located on the clamp second side (122) at the clamp posterior end (126), with the arcuate clamp anterior end (125) joining the clamp first side (121) to the clamp second side (122). In some embodiments, a first ridged and grooved clamping block (131) may be angularly located on the clamp first side posterior end (123) and a second ridged and grooved clamping block (132) may be angularly located on the clamp second side posterior end (124). In some embodiments, the first ridged and grooved clamping block (131) may mate and/or interface with the second ridged and grooved clamping block (132) upon closure of the clamp (120). In some embodiments, the first ridged and grooved clamping block (131) and the second ridged and grooved clamping block (132) may be positioned at a 90 degree angle with respect to the clamp first side (121) and the clamp second side (122), respectively. In some embodiments, the first ridged and grooved clamping block (131) and the second ridged and grooved clamping block (132) may be positioned at a 75 degree angle with respect to the clamp first side (121) and the clamp second side (122), respectively. In some embodiments, the first ridged and grooved clamping block (131) and the second ridged and grooved clamping block (132) may be positioned at a 60 degree angle with respect to the clamp first side (121) and the clamp second side (122), respectively. In some embodiments, the first ridged and grooved clamping block (131) and the second ridged and grooved clamping block (132) may be positioned at a 45 degree angle with respect to the clamp first side (121) and the clamp second side (122), respectively. In some embodiments, the first ridged and grooved clamping block (131) and the second ridged and grooved clamping block (132) may be positioned at a 105 degree angle with respect to the clamp first side (121) and the clamp second side (122), respectively. In some embodiments, the first ridged and grooved clamping block (131) and the second ridged and grooved clamping block (132) may be positioned at a 120 degree angle with respect to the clamp first side (121) and the clamp second side (122), respectively. In some embodiments, the first ridged and grooved clamping block (131) and the second ridged and grooved clamping block (132) may be positioned at a 135 degree angle with respect to the clamp first side (121) and the clamp second side (122), respectively.

In some embodiments, the system (100) may comprise a first side compression member (141). In some embodiments, the first side compression member (141) may be located on an inside surface of the clamp first side (121) next to the first ridged and grooved clamping block (131) and project out and away from the clamp first side (121) toward the clamp second side (122). In some embodiments, the first side compression member (141) may comprise a shape of a rectangular prism. In some embodiments, the first side compression member (141) may be elastomeric.

In some embodiments the first side compression member (141) may be constructed of foam. In some embodiments the first side compression member (141) may be constructed of rubber. In some embodiments the first side compression member (141) may be constructed of latex. In some embodiments the first side compression member (141) may comprise a planar interfacing surface.

In some embodiments, the system (100) may comprise a second side compression member (142). In some embodiments, the second side compression member (142) may be located on an inside surface of the clamp second side (122) next to the second ridged and grooved clamping block (132) and project out and away from the clamp second side (122) toward the clamp first side (121). In some embodiments, the second side compression member (142) may comprise a shape of a rectangular prism. In some embodiments, the second side compression member (142) may be elastomeric.

In some embodiments the second side compression member (142) may be constructed of foam. In some embodiments the second side compression member (142) may be constructed of rubber. In some embodiments the second side compression member (142) may be constructed of latex. In some embodiments the second side compression member (142) may comprise a planar interfacing surface.

In some embodiments, the system (100) may comprise an adjustable ratcheting lock (150) located between and attaching the clamp first side (121) and the clamp second side (122) in a releasable manner. In some embodiments, a ratcheting lock first end (151) may be located on the inside surface of the clamp first side (121) between the clamp first side posterior end (123) and the clamp anterior end (125) and a ratcheting lock second end (152) may be located on the inside surface of the clamp second side (122) between the clamp second side posterior end (124) and the clamp anterior end (125). In some embodiments, the adjustable ratcheting lock (150) may comprise a plurality of settings corresponding to a level of compression between the first side compression member (141) and the second side compression member (142).

In some embodiments, the system (100) may comprise a first finger grip (161) located on an outside surface of the clamp first side (121) opposed to the ratcheting lock first end (151) and a second finger grip (162) located on an outside surface of the clamp second side (122) opposed to the ratcheting lock second end (152).

In some embodiments, medical wire (110) may be placed in an open clamp (120) between the first side compression member (141) and the second side compression member (142). In some embodiments, the clamp (120) may be closed having the first ridged and grooved clamping block (131) interfacing and interlocked against the second ridged and grooved clamping block (132). In some embodiments, the adjustable ratcheting lock (150) may be tightened via manually pinching the clamp (120) via the first finger grip (161)

and the second finger grip (162) to compress the first side compression member (141) and the second side compression member (142) against the medical wire (110) for securely holding the medical wire (110) in position.

In some embodiments, the first side compression member (141) may be located on the inside surface of the clamp first side (121) and the second side compression member (142) may be located on the inside surface of the clamp second side (122). The compression members (141, 142) may be secured to the first and second sides (121, 122) by an adhesive such as a water resistant adhesive, or a saline compatible adhesive.

In some embodiments, the first side compression member (141) may be located on the inside surface of the clamp first side (121) and the second side compression member (142) may be located on the inside surface of the clamp second side (122), wherein the compression members (141, 142) are secured to the first and second sides (121, 122) via a mechanical fastening, such as a bolt, staple, or fingers extending from the first and second sides (121, 122).

In some embodiments, the system (100) may further comprise a medical wire (110).

In some embodiments, the medical wire (110) may be an interventional procedure wire.

In some embodiments, the medical wire (110) may be a cardiac catheterizing wire.

In some embodiments, the medical wire (110) may be a hydrophilic wire.

In some embodiments, the medical wire (110) may be a micro wire.

In some embodiments, the medical wire (110) may be a guide wire.

In some embodiments, the medical wire (110) may be a catheter.

In some embodiments, the system (100) may further comprise a catheter and guide wire bowl. In some embodiments, the system (100) may further comprise a bowl.

In some embodiments, the system (100) may further comprise a plurality of clamps (120). In some embodiments, the system (100) may further comprise a plurality of color coded clamps (120). In some embodiments, the system (100) may further comprise a plurality of labeled clamps (120).

In some embodiments, the system (100) may further comprise an indicator located on each clamp (120) for indicating wire type or size.

In some embodiments, the indicator may be a unique color.

A method of containment and organization of a medical wire may comprise obtaining a system (100) for containment and organization of a medical wire comprising a clamp (120) having a clamp first side (121), a clamp second side (122), a clamp anterior end (125), and a clamp posterior end (126). In some embodiments, the clamp (120) may comprise a shape of a "U". In some embodiments, the clamp (120) may comprise a terminating clamp first side posterior end (123) located on the clamp first side (121) at the clamp posterior end (126), a terminating clamp second side posterior end (124) located on the clamp second side (122) at the clamp posterior end (126), with the arcuate clamp anterior end (125) joining the clamp first side (121) to the clamp second side (122). In some embodiments, a first ridged and grooved clamping block (131) may be angularly located on the clamp first side posterior end (123) and a second ridged and grooved clamping block (132) may be angularly located on the clamp second side posterior end (124). In some embodiments, the first ridged and grooved clamping block (131) may mate with and/or interface with the second ridged and grooved clamping block (132) upon closure of the clamp (120). In some embodiments, the system (100) may comprise a first side compression member (141). In some embodiments, the first side compression member (141) may be located on an inside surface of the clamp first side (121) next to the first ridged and grooved clamping block (131) and projects out and away from the clamp first side (121) toward the clamp second side (122). In some embodiments, the first side compression member (141) may comprise a shape of a rectangular prism. In some embodiments, the first side compression member (141) may be elastomeric. In some embodiments, the system (100) may comprise a second side compression member (142). In some embodiments, the second side compression member (142) may be located on an inside surface of the clamp second side (122) next to the second ridged and grooved clamping block (132) and projects out and away from the clamp second side (122) toward the clamp first side (121). In some embodiments, the second side compression member (142) may comprise a shape of a rectangular prism. In some embodiments, the second side compression member (142) may be elastomeric. In some embodiments, the system (100) may comprise an adjustable ratcheting lock (150) located between and releasably attaching the clamp first side (121) and the clamp second side (122). In some embodiments, a ratcheting lock first end (151) may be located on the inside surface of the clamp first side (121) between the clamp first side posterior end (123) and the clamp anterior end (125) and a ratcheting lock second end (152) is located on the inside surface of the clamp second side (122) between the clamp second side posterior end (124) and the clamp anterior end (125). In some embodiments, the system (100) may comprise a first finger grip (161) located on an outside surface of the clamp first side (121) opposed to the ratcheting lock first end (151) and a second finger grip (162) located on an outside surface of the clamp second side (122) opposed to the ratcheting lock second end (152). In some embodiments, the system (100) may comprise a medical wire (110). In some embodiments, the system (100) may comprise a catheter and guide wire bowl.

In some embodiments, the method may comprise removing the medical wire (110) from its sterile packaging.

In some embodiments, the method may comprise placing the medical wire (110) in an open clamp (120) between the first side compression member (141) and the second side compression member (142) in either a straight or a looped position having at least one strand of the medical wire (110) in contact with the first side compression member (141) and the second side compression member (142).

In some embodiments, the method may comprise closing the clamp (120) with the first ridged and grooved clamping block (131) interfacingly interlocked against the second ridged and grooved clamping block (132).

In some embodiments, the method may comprise tightening the clamp (120) with the adjustable ratcheting lock (150) via manually pinching the clamp (120) via the first finger grip (161) and the second finger grip (162) to compress the first side compression member (141) and the second side compression member (142) against the medical wire (110) for securely holding into position.

In some embodiments, the method may comprise placing the clamp (120) with the medical wire (110) into the catheter and guide wire bowl in preparation for use.

In some embodiments, the method may comprise discarding the clamp (120) after a single use.

In some embodiments, the method may comprise a plurality of clamps (120) used with a plurality of medical wires (110). In some embodiments, the plurality of clamps (120) may comprise a unique indicator located on each clamp (120) for indicating wire type or size. These unique indicators may assist in identifying the each clamp (120) and the associated medical wire (110) restrained by the clamp (120).

Figure 2:
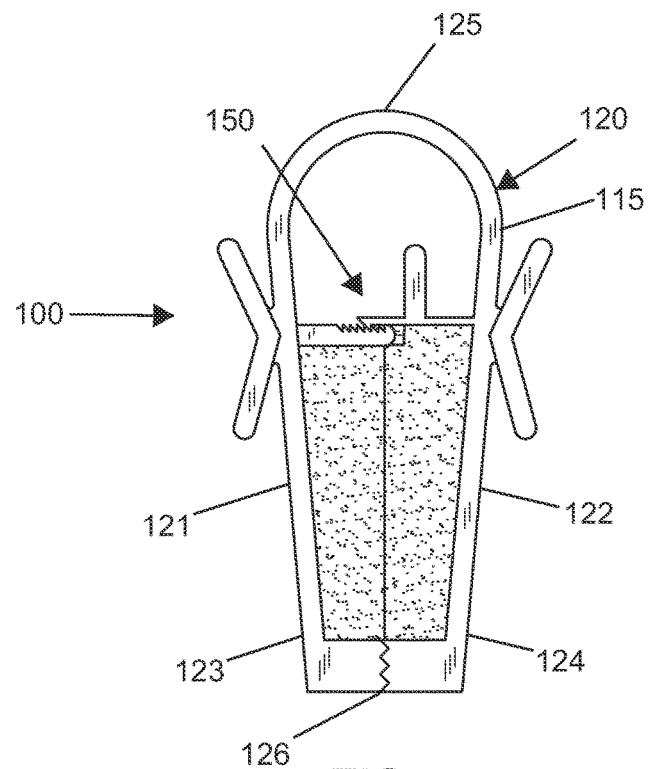
FIG. 2 shows a front view of the embodiment, in the closed position.
Figure 3:
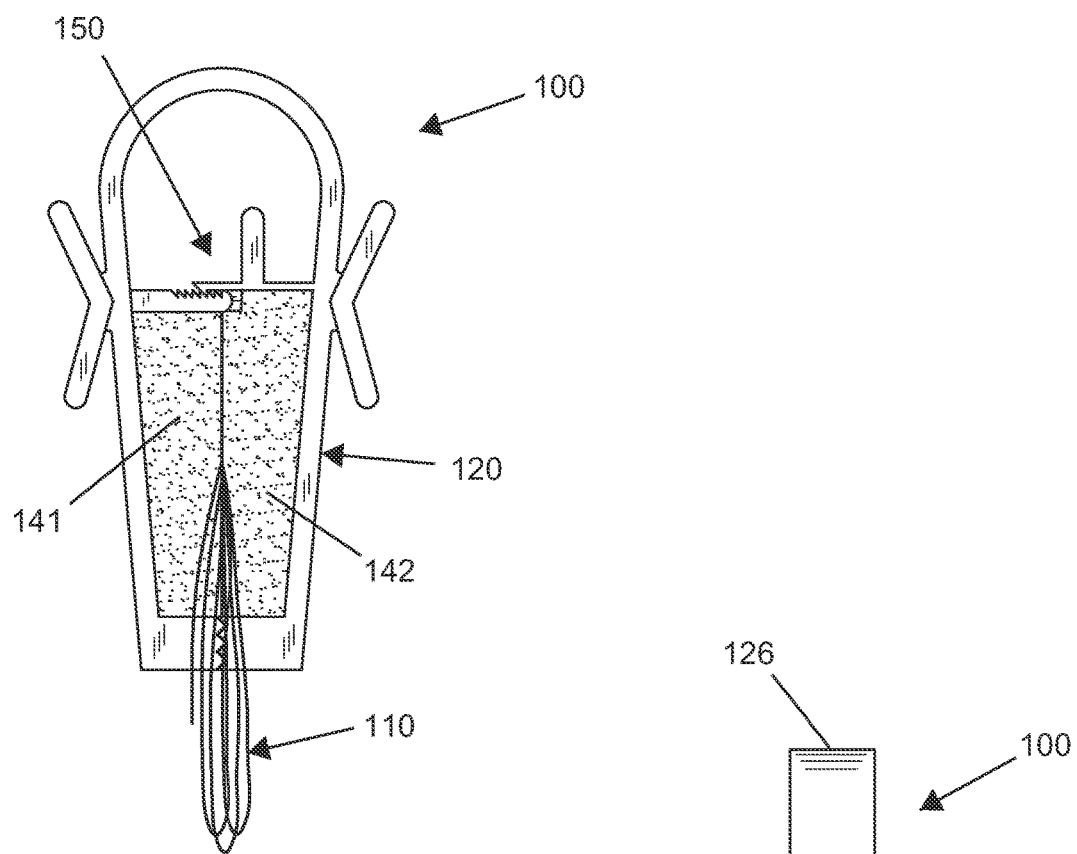
FIG. 3 shows a front view of the embodiment, in the open position, with a medical wire.
Figure 4:
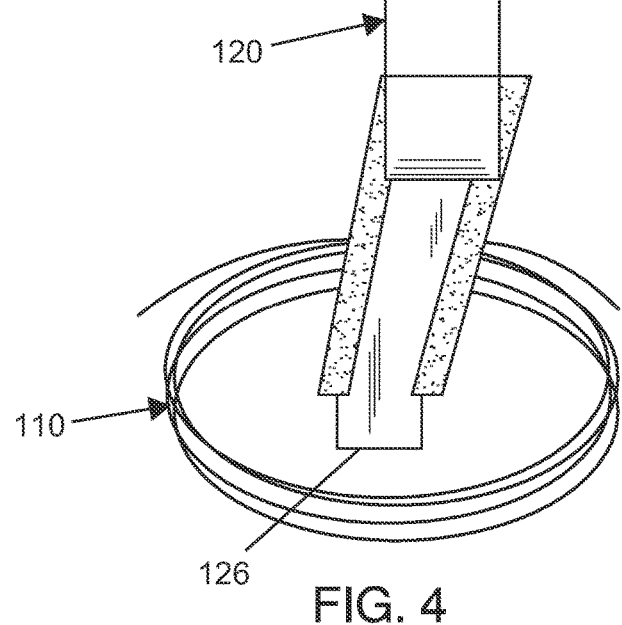
FIG. 4 shows a side view of the embodiment, in the closed position, with a medical wire.
Figure 5:
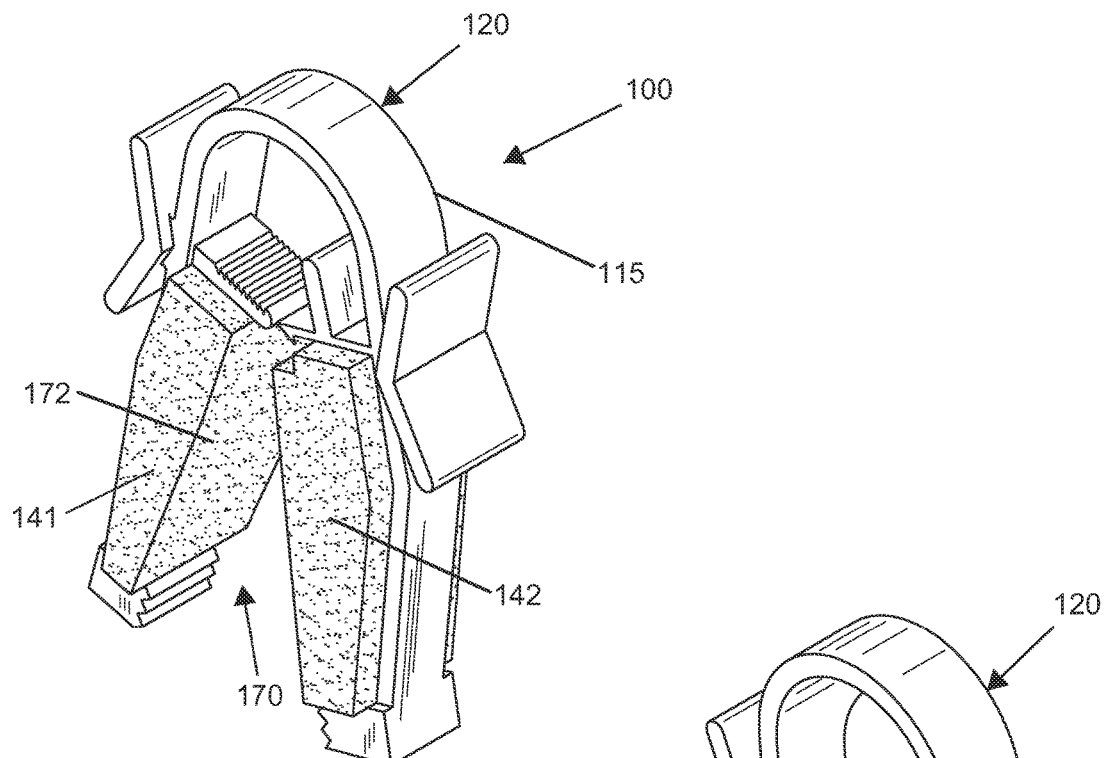
FIG. 5 shows a perspective view of the embodiment, in the open position.
Figure 6:
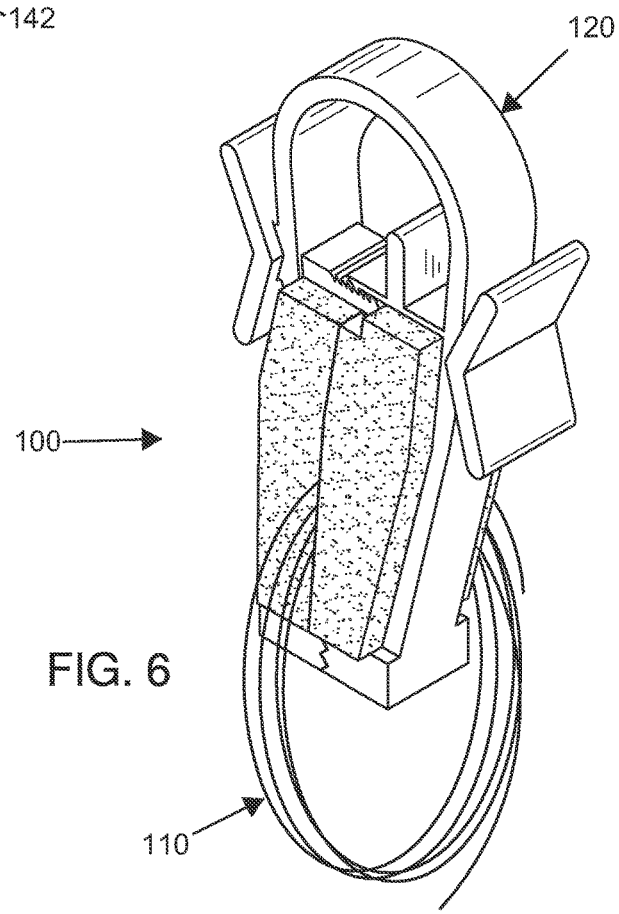
FIG. 6 shows a perspective view of the embodiment, in the closed position, with a medical wire.

In another embodiment, the clamp (120) may comprise a body (115) having the first side element (121) and the second side element (122). The first side element (121) and the second side element (122) may be connected by an anterior end (125). The body (115) of the clamp (120) may be movable from an open position to a closed position. When the body (115) is in the open position, as shown in FIG. 1, the first side element (121) and the second side element (122) are separated by a gap (170). When the body (115) is in the closed position, as shown in FIG. 2, the first side element (121) and the second side element (122) may be closer together, and may have even closed the gap (170).

The first compression member (141) may be coupled to the inner surface of the first side element (121), and the second compression member (142) may be coupled to the inner surface of the second side element (122). The first and second compression members (141, 142) may project inwardly from the respective first and second side elements (121, 122), and may comprise a respective first surface (172) and a second surface (174) arranged such that when a medical wire is positioned in the gap (170) between the first surface and the second surface, the body (115) may be moved to the closed position. When or before the body (115) reaches the closed position, at least one of the first and second compression members (141, 142) may deform to accommodate the medical wire (110). This deformation may occur due to compression of one or both of the compression members (141, 142). While the body (115) remains in the closed position, the movement of the medical wire (110) in or out of the clamp (120) may be restricted between the first and second compression members (141, 142). The internal resistance of the first and second compression members (141, 142) to compression or deformation may apply a force to the medical wire (110) to restrict its movement and hold it in place.

Figure 7:
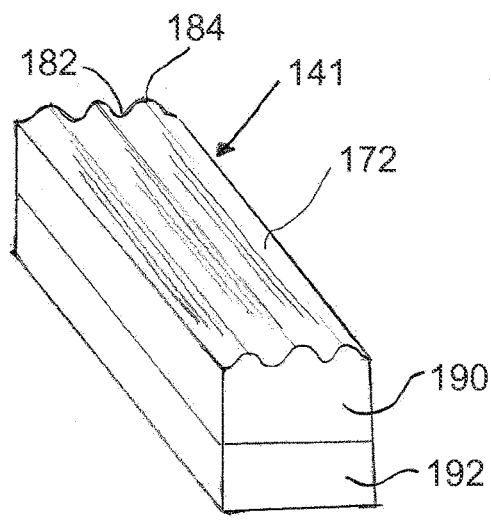
FIG. 7 shows a perspective view of another embodiment of a compression member.

The first and second compression members (141, 142) may be made of a material such that the first and second compression members (141, 142) are responsive to deform when a force between 0.25 pounds and 5.0 pounds is applied. The first and second compression members (141, 142) may comprise a foam material, such as a sponge, a rubber material, or some other deformable material. To prevent fragments of the first and second compression members (141, 142) from breaking off and attaching to the medical wire (110), it may be advantageous that the first and second compression members (141, 142) comprise closed cell foam, wherein the empty cells within the foam's interior are not exposed on the first or second surfaces (172, 174). Alternatively, open cell foam may be advantageous where greater deformation of the first and second compression members (141, 142) is needed with less force being applied. In some embodiments, it may be advantageous that the first and second compression members (141, 142) are each made from different materials (190, 192) having different compressive abilities, as shown in FIG. 7. Such an embodiment may be useful where, for example, it is desirable that the medical wire (110) should be forced closer to the first side element (121) or second side element (122) when the body (115) is placed in the closed position.

The first and second compression members (141, 142) may be arranged on the inner surface of the respective first and second side elements (121, 122) projecting inwardly to a maximum thickness. This thickness may be between about 0.3 cm and 1.5 cm. Compression members (141, 142) having greater thickness may be advantageous to allow for greater deformation or compression when receiving the medical wire (110) and therefore, maintain a better grip on the medical wire (110) contained between the compression members (141, 142). The thickness of the compression members (141, 142) may be limited so that they do not completely occlude the gap (170) when the body (115) is in the open position, so that the medical wire (110) may still be easily moved between the first and second compression members (141, 142) while the body (115) is in the open position.

Figure 8:
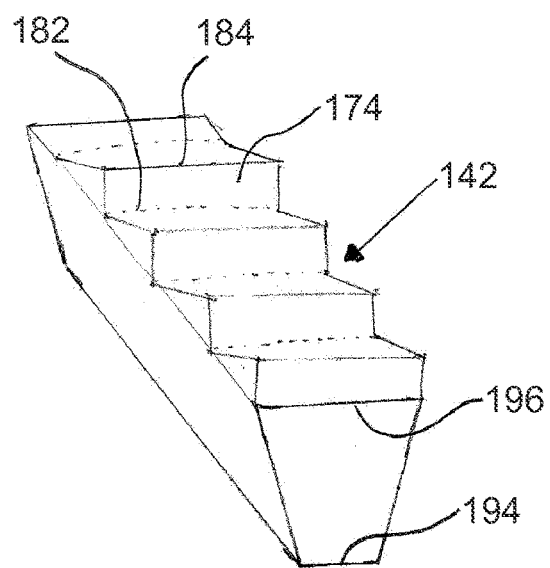
FIG. 8 shows a perspective view of another embodiment of a compression member.

The first and second compression members (141, 142) may also have a width between about 0.3 cm and 1.4 cm. Compression members (141, 142) having greater width may be able to better secure the medical wire (110). Therefore, it may be advantageous that the compression members (141, 142) have a width which exceeds the width of the first and second side elements (121, 122). Alternatively, it may be desirable that the compression members (141, 142) have a "wedge-shape", wherein the width expands as the compression member (141, 142) extends inwardly, as shown in FIG. 8. In such an embodiment, the width of the first and second surfaces (172, 174) may define the maximum width (196) of the compression members (141, 142).

The thickness of the first and second compression members (141, 142) may vary from the posterior end to the anterior end of the compression members (141, 142). Such variation may be advantageous to allow the surfaces (172, 174) of the compression members (141, 142) to be substantially coplanar when the body (115) is placed in the closed position. Accordingly, the gap (170) between the compression members (141, 142) while the body (115) is in the open position may also vary. For embodiments similar to FIG. 1, the gap (170) is likely to be larger on the posterior side of the compression members (141, 142), and smaller on the anterior side of the compression members (141, 142). The size of the gap may vary between about 0.1 cm and 1.7 cm. Similarly, the thickness of the compression members (141, 142) may vary from the posterior end to the anterior of the compression members (141, 142). As shown in FIG. 1, the anterior end of the compression members (141, 142) may have the maximum thickness and the posterior end of the compression members (141, 142) may have the minimum thickness. The compressibility of the compression members (141, 142) may vary according to the thickness of the compression members (141, 142).

Additionally, it may be desirable that the first and second compression members (141, 142) have different widths, so that when the first and second compression members (141, 142) contact one another, the wider of the first and second surfaces (172, 174) covers the entire width of the narrower of the first and second surfaces (172, 174). The wider of the first and second surfaces may also extend beyond the width of the narrower surface (172, 174). Therefore, when body (115) is moved to the closed position so that when the medical wire (110) is restrained between the compression members (141, 142), a first restricting force is directed on the medical wire (110) directed on the portion of the medical wire (110) which overlaps both compression members (141, 142). Additionally, a second force may also be directed to where the medical wire (110) overlaps the portion of the wider surface (172, 174) but not overlapping the narrower surface (172, 174).

In some embodiments, it may be desirable that at least one of the first and second compression members (141, 142)

comprise a plurality of materials (190, 192) stacked inwardly upon each other, where each of the plurality of materials (190, 192) has a different compressibility. For example, an embodiment could comprise one or both compression members (141, 142) having a contacting material (190) which is stacked inward from a base material (192). Depending on the function of the compression members (141, 142) and the characteristics of the medical wire (110) the compression members (141, 142) are configured to receive, one of the materials (190, 192) may have a greater compressibility than the other material (190, 192). In an embodiment where the contacting material (190) has greater compressibility, the compression members (141, 142) may easily conform to the shape of the medical wire (110) when the body (115) is placed in the closed position and resist the movement of the medical wire (110) in the vertical direction as well as the length-wise direction. Alternatively, an embodiment where the base material (192) has greater compressibility may be desirable. Such an arrangement may reduce the amount by which the compression members (141, 142) would conform to the shape of the medical wire (110), however, it may also allow for substantial compression while applying the force of compression more evenly across the first and second surfaces (172, 174) of the compression members (141, 142). This may be desirable where the first and second surfaces (172, 174) are arranged to capture the medical wire (110) in a groove (182) or receiving element. In some embodiments, similar effects as those described above may be accomplished by compression members (141, 142) having more than two materials (190, 192), or by compression members (141, 142) having a compressibility gradient which varies with the thickness of the compression member (141, 142).

The first and second surfaces (172, 174) may comprise a surface treatment to better capture and restrain the medical wire (110) while the body (115) is in the closed position. The surface treatment may be a coating with a material having a high coefficient of friction, a collection of surface irregularities, such as pits and projections, arranged on the first and second surfaces (172, 174), or a series of grooves (184) and ridges (182) arranged along a portion of the first and second surfaces (172, 174).

One of the first or second surfaces (172, 174) may comprise a series of grooves (184) and ridges (182). The other of the first and second surfaces (172, 174) may be flat, or may comprise another series of grooves (184) and ridges (182). Where there are grooves (184) and ridges (182) on both the first and second surfaces (172, 174), it may be desirable that these grooves (184) interlock, causing the gap (170) to be completely closed when the body (115) is placed in the closed position. The medical wire (110) may be placed within the clamp (120) spanning the width of the first and second surfaces (172, 174). The grooves (184) and ridges (182) alternatively may be arranged to span the length or a portion of the length of the first or second surface (172, 174) to apply the force of compression to focused areas of the medical wire (110), as shown in FIG. 7. Alternatively, the grooves (184) and ridges (182) may be arranged to span the width or a portion of the width of the first and second surfaces (172, 174) to capture the medical wire (110) within the groove (184) and restrain the lengthwise movement of the medical wire (110), as shown in FIG. 8. Additionally, where the grooves (184) and ridges (182) are arranged spanning the width of the first and second surfaces (172, 174), it may be desirable that the grooves (184) and ridges (182) are arranged in a planform arc across the width of the first and second surfaces (172, 174) so that the coiled medical wire (110) may be accommodated within the grooves (184). Furthermore, it may be desirable that the grooves (184) and ridges (182) have varying arcs to accommodate coils of medical wires (110) having varying diameters.

As discussed above, some embodiments of the clamp (120) may comprise clamping blocks (123, 124) extending inwardly from the posterior end of the first and second side elements (121, 122). The clamping blocks (123, 124) may be made of a substantially rigid material and the inward end of each clamping block (123, 124) may be in contact when the body (115) is moved to the closed position. The inward end of each clamping block (123, 124) may define the limit of the movement of the body (115) to the closed position. While the body (115) is in the closed position, the clamping blocks (123, 124) may define a rigid wall which prevents movement of the medical wire (110) from passing through the posterior end (126) of the clamp (120). To further accomplish this purpose, the inward ends of the clamping blocks (123, 125) may comprise interlocking grooves.

In some embodiments, at least one of the compression members (141, 142) may extend inward beyond the inward ends of the clamping blocks (123, 124). The result of this arrangement of the compression members (141, 142) is that when the body (115) is moved to the closed position, there will be at least some compression of the compression members (141, 142) even where no medical wire (110) is placed between the compression members (141, 142).

In some embodiments, it may be desirable that the first and second compression members (141, 142) make substantially planar contact with each other as the body (115) is moved to the closed position. Substantially planar contact may mean that the entirety of the surfaces (172, 174) of the compression members (141, 142) which overlap while the body (115) is in the closed position, come in contact with each other substantially simultaneously as the body (115) is moved to the closed position. An advantage of this may be that such an arrangement may provide even compression between the compression members (141, 142) and may distribute compression evenly across the first and second surfaces (172, 174). Even distribution of the compression of the compression members (141, 142) may more effectively restrain the movement of the medical wire (110) by restraining it in a particular spot between the compression members (141, 142). Alternatively, the compression members (141, 142) may be arranged such that the posterior or anterior ends of the surfaces (172, 174) of the compression members (141, 142) make contact before other areas of the surfaces (172, 174). Such an embodiment may cause unequal compression of the compression members (141, 142) and may be desirable to apply additional force to one of the anterior or posterior ends of the compression member (141, 142) and prevent movement of the medical wire (100) disposed between the compression members (141, 142) in a specific direction.

In some embodiments, it may be desirable that the body (115) of the clamp (120) is biased to the open position, such that unless force is being applied to the clamp (120), the clamp (120) is able to receive the medical wire (110) between the compression members (141, 142). Furthermore, to restrain the movement of the captured medical wire (110) between the compression members (141, 142) while the body (115) is in the closed position, it may be desirable to include a lock coupled to the body (115) of the clamp (120) to maintain the body (115) in the closed position. The lock may comprise a number of mechanisms adapted to maintain the body (115) in the closed position, such as the ratcheting lock (150) described above. To avoid interfering with the positioning of the medical wire (110) in the gap (170), it may be advantageous to position the lock in a position anterior from the compression members (141, 142).

As used herein, the term "about" refers to plus or minus 10% of the referenced number.

Various modifications, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions using the phrase "comprising" includes embodiments that could be described as "consisting of", and as such the written description requirement for claiming one or more embodiments using the phrase "consisting" of is met.

We claim:

1. A clamp comprising:
    a body comprising a first side element and a second side element connected to one another at an anterior end, wherein the body is movable from an open position to a closed position;
    a first compression member coupled to an inner surface of the first side element and having a first surface; and
    a second compression member coupled to a second inner surface of the second side element and having a second surface;
    wherein the first surface and the second surface are arranged such that when a medical wire is positioned between the first surface and the second surface, and the body is moved to the closed position, the first surface and the second surface contact one another and at least one of the first compression member and the second compression member deform to restrain the medical wire; and
    wherein the first compression member and the second compression member each have a width which is larger than a width of the first side element and a width of the second side element.

2. The clamp of claim 1, wherein the first side element comprises a first clamping block extending inwardly from a first posterior end of the first side element, and the second side element comprises a second clamping block extending inwardly from a second posterior end of the second side element, and wherein the first clamping block and the second clamping block are in contact with one another when the body is in the closed position.

3. The clamp of claim 2, wherein the first clamping block and the second clamping block comprise interlocking ridges and grooves.

4. The clamp of claim 2, wherein at least one of the first compression member and the second compression member extend inwardly further than the respective first clamping block or second clamping block.

5. The clamp of claim 1, wherein at least one of the first compression member and the second compression member deform when the body is moved to the closed position when a medical wire is not present.

6. The clamp of claim 1, wherein the body is arranged such that as the body is moved toward the closed position, the first surface of the first compression member and the second surface of the second compression member make substantially planar contact with each other.

7. The clamp of claim 1, wherein at least one of the first surface and the second surface comprises a surface treatment configured to restrict movement of the medical wire while the body is in the closed position.

8. The clamp of claim 7, wherein the surface treatment comprises a plurality of interlocking ridges and grooves, each of the interlocking ridges and grooves arranged lengthwise on each of the first surface and the second surface.

9. The clamp of claim 7, wherein the surface treatment comprises a plurality of interlocking ridges and grooves, each of the interlocking ridges and grooves arranged widthwise on each of the first surface and the second surface.

10. The clamp of claim 9, wherein the interlocking ridges and grooves form a planform arc configured to accommodate a coiled medical wire.

11. The clamp of claim 1, wherein the body is biased towards the open position.

12. The clamp of claim 11, wherein the body further comprises a lock to maintain the body in the closed position.

13. The clamp of claim 1, wherein the first compression member and the second compression member are responsive to deform when a force between about 0.25 pounds and 5.0 pounds is applied.

14. The clamp of claim 1, wherein the first compression member and the second compression member comprise closed cell foam.

15. A clamp comprising:
    a body comprising a first side element and a second side element connected to one another at an anterior end, wherein the body is movable from an open position to a closed position;
    a first compression member coupled to an inner surface of the first side element and having a first surface; and
    a second compression member coupled to a second inner surface of the second side element and having a second surface;
    wherein the first surface and the second surface are arranged such that when a medical wire is positioned between the first surface and the second surface, and the body is moved to the closed position, the first surface and the second surface contact one another and at least one of the first compression member and the second compression member deform to restrain the medical wire,
    wherein each of the first compression member and the second compression member have a width which increases extending inwardly.

16. A system for restraining a medical wire comprising:
    a plurality of clamps, each of the plurality of clamps comprising a body comprising a first side element and a second side element connected to one another at an anterior end, wherein the body is movable from an open position to a closed position, a first compression member coupled to an inner surface of the first side element and having a first surface, and a second compression member coupled to a second inner surface of the second side element and having a second surface, wherein the first surface and the second surface are arranged such that when the body is moved to the closed position, the first compression member is in contact with the second compression member and both the first compression member and the second compression member are compressed; and wherein each of the plurality of clamps has a unique identifying element; and wherein each of the first compression member and the second compression member have a width which increases extending inwardly.

17. The system of claim 16, wherein each of the plurality of clamps further comprises a lock positioned on the body posterior from the first compression member and the second compression member wherein the lock maintains the body in the closed position.

18. A clamp comprising;

a body comprising a first side element having a first clamping block extending inwardly from a first posterior end of the first side element, and a second side element having a second clamping block extending inwardly from a second posterior end of the second side element; wherein the first side element and the second side element are connected to one another at an anterior end, and wherein the body is movable from an open position to a closed position;

a first compression member coupled to an inner surface of the first side element and having a first surface;

a second compression member coupled to a second inner surface of the first side element and having a second surface;

wherein the closed position is defined by an arrangement wherein the first clamping block is in contact with the second clamping block, and wherein the first compression member is in contact with the second compression member when the body is in the closed position; and wherein at least one of the first compression member or the second compression member comprises a plurality of materials stacked inwardly upon each other, each of the plurality of materials having a different compressibility.

19. The clamp of claim 18, wherein the body further comprises a first grip arranged on a first outer surface of the first side element, and a second grip arranged on a second outer surface of the second side element.

20. The clamp of claim 18, wherein the first compression member and the second compression member have different widths.

* * * * *